US00PP29661P3

(12) United States Plant Patent
Suphachadiwong

(10) Patent No.: US PP29,661 P3
(45) Date of Patent: Sep. 11, 2018

(54) ***VANDA* PLANT NAMED 'SPCDW1524'**

(50) Latin Name: ***Vanda* Jones ex R. Br.**
Varietal Denomination: SPCDW1524

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 11 days.

(21) Appl. No.: 15/530,123

(22) Filed: Dec. 5, 2016

(65) Prior Publication Data

US 2017/0172043 P1 Jun. 15, 2017

(30) Foreign Application Priority Data

Dec. 9, 2015 (QZ) ..... PBR 2015/2979

(51) Int. Cl.
*A01H 5/02* (2018.01)

(52) U.S. Cl.
USPC ..... Plt./311

(58) Field of Classification Search
USPC ..... Plt./311
See application file for complete search history.

*Primary Examiner* — Keith O. Robinson
(74) *Attorney, Agent, or Firm* — Samuel R. McCoy, Jr.

(57) ABSTRACT

A new and distinct *Vanda* cultivar named 'SPCDW1524' which is characterized by a small plant size, large flowers, yellow lateral petals which are heavily dotted greyed-purple, a yellow dorsal sepal which is heavily dotted greyed-purple, yellow lateral sepals which are heavily dotted and striped greyed-purple, a labellum with yellow lateral lobes and a central lobe which is colored greyed-red and margined greyed-orange, and the stability of these characteristics from generation to generation.

4 Drawing Sheets

Latin name of the genus and species: The Latin name of the genus and species of the novel variety disclosed herein is *Vanda* Jones ex R. Br..

Variety denomination: The inventive variety of *Vanda* disclosed herein has been given the variety denomination 'SPCDW1524'.

CROSS REFERENCE TO RELATED APPLICATIONS

This application claims priority to the Community Plant Variety Rights application number 2015/2979, filed Dec. 9, 2015, which is herein incorporated by reference.

BACKGROUND OF THE INVENTION

Parentage: The *Vanda* variety 'SPCDW1524' is the result of a planned breeding program. The new variety originated as a seedling from the crossing of *Vanda* 'YSRBPM' (not patented), the seed parent, with *Vanda* 'M38BP1' (not patented), the pollen parent. Both parents were developed by, and are owned by, the inventor and were never commercially released. The crossing was made by the inventor in his research greenhouse in Bangphra, Thailand in January of 2005.

The new variety was first selected in December of 2009, in a research greenhouse in Bangphra, Thailand belonging to the inventor. After identifying the new variety as a potentially interesting selection, the inventor continued confidential testing and propagation of 'SPCDW1524', assessing stability of the unique characteristics of this variety.

Asexual Reproduction: Asexual reproduction of the new cultivar 'SPCDW1524', by way of mericloning, was first initiated in May of 2010 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1524' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1524'. These characteristics in combination distinguish 'SPCDW1524' as a new and distinct *Vanda* cultivar:

1. *Vanda* 'SPCDW1524' exhibits a small plant size; and
2. *Vanda* 'SPCDW1524' exhibits large flowers; and
3. *Vanda* 'SPCDW1524' exhibits yellow sepals and lateral petals; and
4. *Vanda* 'SPCDW1524' exhibits lateral petals which are heavily dotted greyed-purple; and
5. *Vanda* 'SPCDW1524' exhibits a dorsal sepal which is heavily dotted greyed-purple, and lateral sepals which are heavily dotted and striped greyed-purple; and
6. *Vanda* 'SPCDW1524' exhibits a labellum with a central lobe which is colored greyed-red and margined greyed-orange, and yellow lateral lobes.

BOTANICAL DESCRIPTION OF THE PLANT

Figure 1:
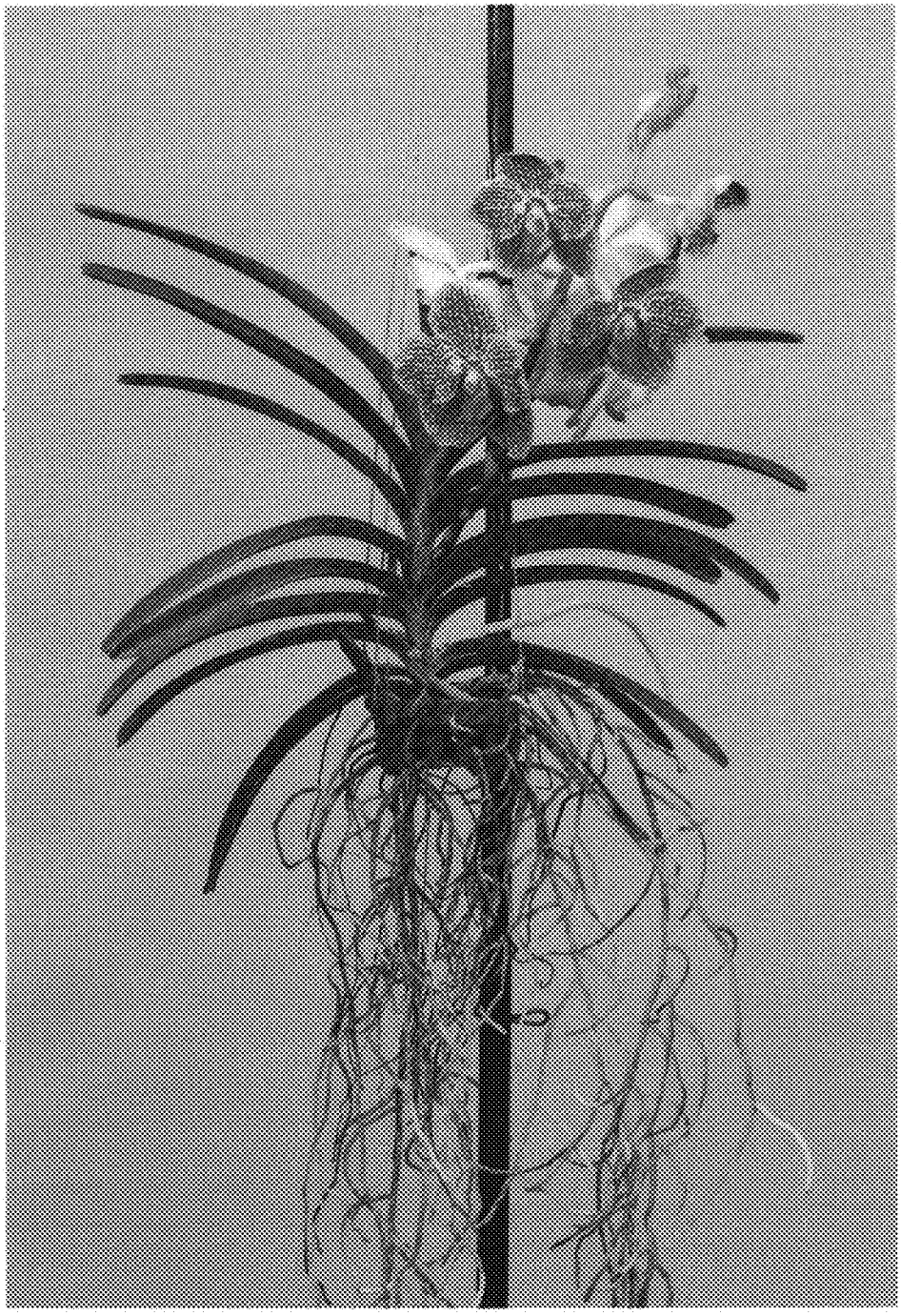
FIG. 1 illustrates, as nearly true as it is reasonably possible to make the same in color photographs of this type, an exemplary plant of 'SPCDW1524' grown in a commercial greenhouse in Honselersdijk, the Netherlands. This plant is approximately 6 years old from the time of mericloning, shown planted in an 8 by 8 cm container.
Figure 2:
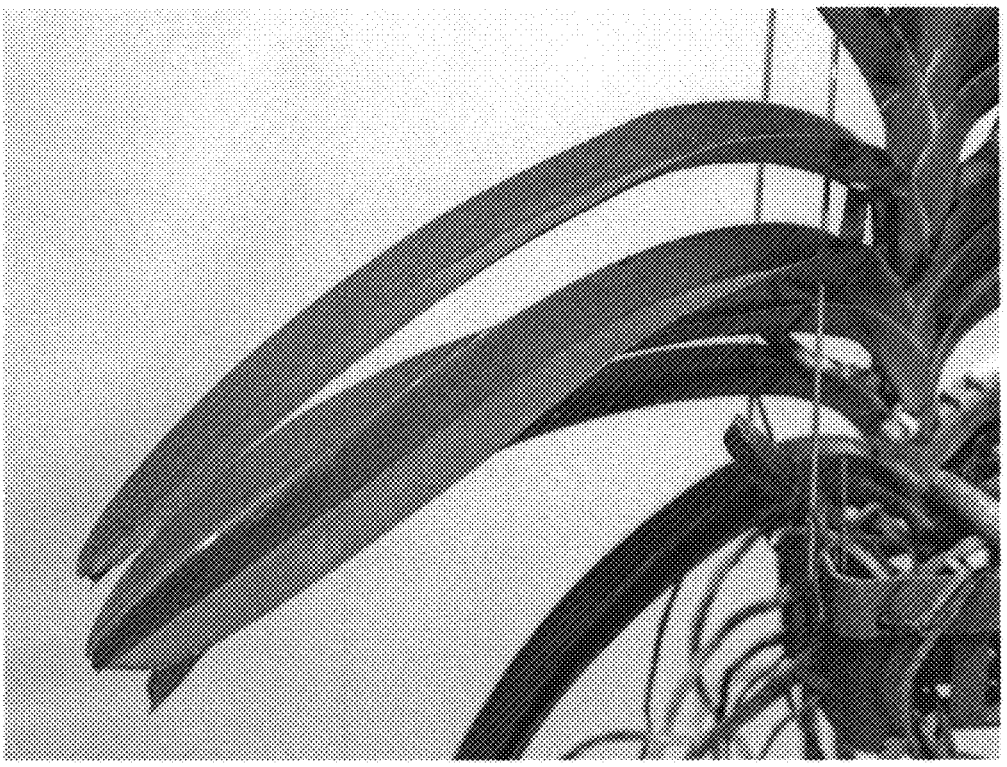
FIG. 2 illustrates, as nearly true as it is reasonably possible to make the same in color photographs of this type, the typical foliage of 'SPCDW1524'.
Figure 3:
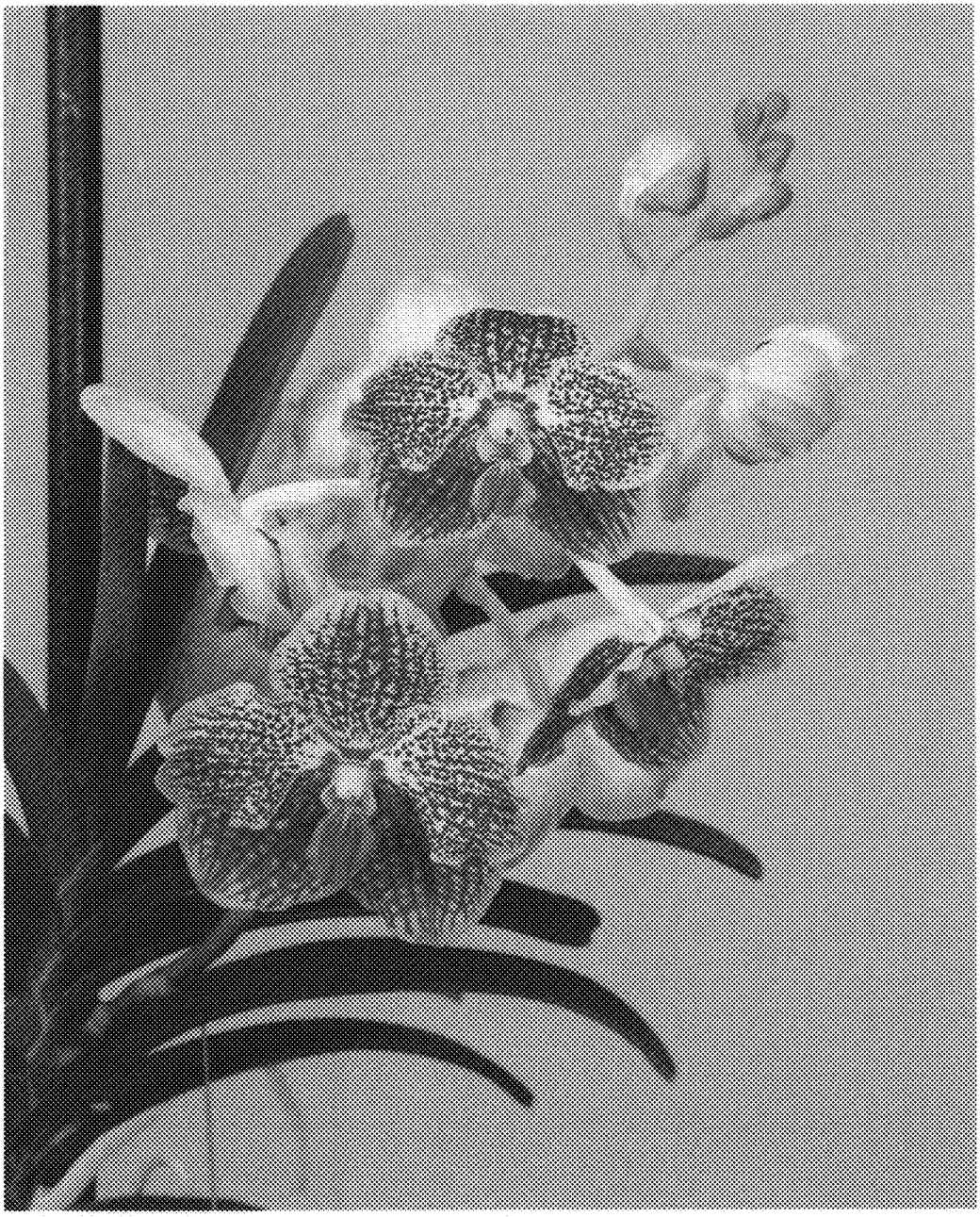
FIG. 3 illustrates, as nearly true as it is reasonably possible to make the same in color photographs of this type, the typical inflorescence of 'SPCDW1524'.
Figure 4:
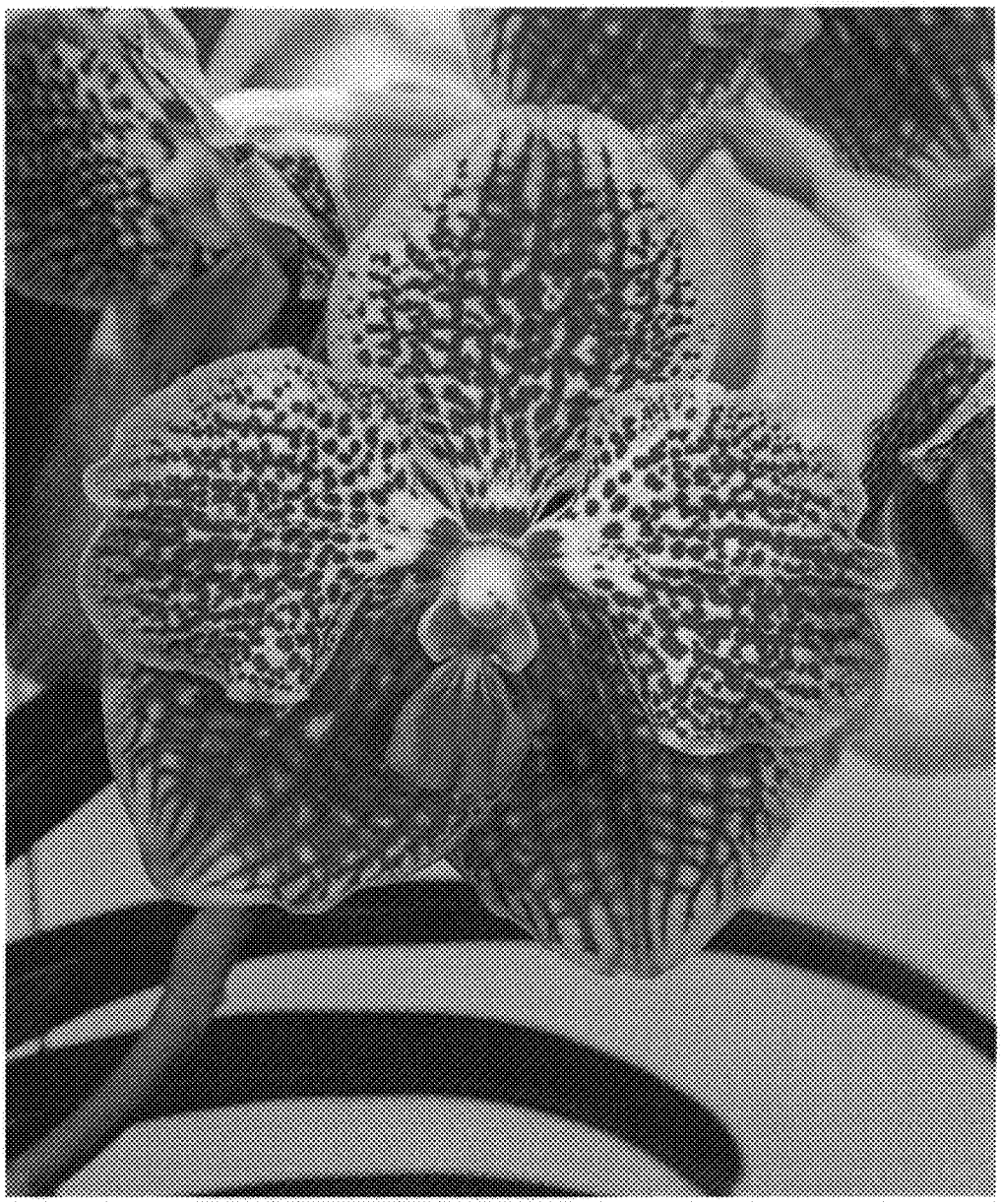
FIG. 4 illustrates, as nearly true as it is reasonably possible to make the same in color photographs of this type, the typical flower of 'SPCDW1524'.

The following observations and measurements made in November of 2016 describe averages from a sample set of six specimens of six year-old 'SPCDW1524' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1524' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1524' and comparisons with other varieties of *Vanda* are provided below.

Plant description:

- *Growth habit*.—Perennial; monopodial, upright. Single monopodial leafy stem, with flowers carried slightly above the leaf plane; inflorescences growing from the leaf axils.
- *Average height from base (plant grown in hanging basket, so no soil line present) to foliar plane*.—33.2 cm.
- *Average height from base (plant grown in hanging basket, so no soil line present) to top of floral plane*.—40.0 cm.
- *Plant spread*.—Average of 40.5 cm.
- *Appropriate container size*.—8 cm by 8 cm rectangular hanging basket.
- *Growth rate*.—Low to moderate.
- *Plant vigor*.—Moderate.
- *Propagation type*.—Meristematic tissue culture propagation using the base of the leaves.
- *Propagation details*.—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility*.—Plants have not been observed to be susceptible or resistant to pathogens and pests common to *Vanda*.
- *Environmental tolerances*.—Adapt to, at least, USDA Zones 11 and 12 and temperatures as high as 40 degrees Celsius; high tolerance to rain; moderate to high tolerance to wind.

Root system:

- *General*.—Densely rooting; with aerial roots only.
- *Dimensions, mature roots*.—45.6 cm long with a diameter of 0.4 cm, on average.
- *Texture*.—Very fleshy; non-fibrous.
- *Color*.—Greyed-green, a mixture of RHS 192A and 192C; root apex is yellow-green, RHS 146A.

Stem:

- *Branching habit*.—Monopodial; no lateral branches present.
- *Number of primary (main) stems per plant*.—One.
- *Number of secondary (lateral) branches per plant*.—None.
- *Appearance and shape*.—Circular, formed by the leaf sheaths.
- *Length*.—16.9 cm.
- *Diameter*.—1.0 cm.
- *Internode length*.—0.8 cm.
- *Luster*.—Slightly glossy.
- *Aspect, main stem*.—Near vertical.
- *Strength*.—Very strong.
- *Color, juvenile*.—Yellow-green, in between RHS 150C and 150D.
- *Color, mature*.—Yellow-green, in between RHS 150C and 150D.
- *Color at internodes*.—Yellow-green, in between RHS 150C and 150D.
- *Pubescence*.—Glabrous.

Foliage:

- *Arrangement*.—Distichous.
- *Dimensions*.—21.3 cm long, excluding the sheath, and 2.0 cm wide.
- *Shape of blade*.—Ligulate; strongly carinate.
- *Aspect*.—Moderately to strongly curved.
- *Apex*.—Unequal praemorse.
- *Base*.—Sheathing.
- *Sheath dimensions*.—4.1 cm long and 1.4 cm wide, on average.
- *Sheath color*.—Yellow-green, nearest to RHS 144D.
- *Margin*.—Entire.
- *Pubescence, texture and luster of adaxial surface*.—Glabrous, smooth, and very slightly glossy.
- *Pubescence, texture and luster of abaxial surface*.—Glabrous, smooth, and matte.
- *Color*.—Variegation — Absent. Juvenile foliage, adaxial surface — Green, nearest to RHS 137B, and suffused with a darker shade of green towards the margins and apex, nearest to RHS NN137B. Juvenile foliage, abaxial surface — Yellow-green, nearest to RHS 146B, and suffused with a darker shade of green towards the margins and apex, nearest to RHS NN137B. Mature foliage, adaxial surface — Green, nearest to RHS NN137A. Mature foliage, abaxial surface — Yellow-green, nearest to RHS 146B, and suffused with a darker shade of green towards the margins and apex, nearest to RHS NN137B.

*Venation*.—Parallel.

*Venation color, adaxial surface*.—Green, nearest to RHS NN137A.

*Venation color, abaxial surface*.—Green, RHS 143A.

*Petiole*.—No petioles present; leaves sessile.

Inflorescence:

*Inflorescence arrangement*.—Axially placed raceme.

*Natural flowering season*.—Autumn into winter.

*Time to flower*.—Approximately 10 months.

*Quantity of inflorescence per plant*.—One.

*Flowers per inflorescence*.—Average of 13.

*Flowers per plant*.—9 open flowers and 4 flower buds.

*Inflorescence height*.—Approximately 21.9 cm (measured from base of lowest flower to top of upper flower).

*Inflorescence diameter*.—Approximately 16.7 cm.

*Peduncle*.—Dimensions — Approximately 30.7 cm long and 0.6 cm wide. Aspect — Generally at a 40 degree angle to lateral branch axis. Strength — Moderately strong. Texture and luster — Glabrous and moderately glossy. Color — Green, nearest to RHS 143B.

Bud:

*Length*.—Average of 1.2 cm.

*Diameter*.—Average horizontal diameter is 1.4 cm; the vertical diameter is 1.4 cm.

*Shape*.—Cubic, with a deltoid apex which is pointed downward.

*Pubescence, texture and luster*.—Glabrous, smooth and slightly glossy.

*Color*.—Yellow-green, in between RHS 152B and 152C, and lighter towards the base, nearest to RHS 151A.

Flower:

*Flower type*.—Zygomorphic (orchidaceous), typical shape for the genus *Vanda*.

*Flowering habit*.—Moderate.

*Shape*.—Zygomorphic, single; consisting of three sepals and three petals, one of which is transformed into a labellum; the two lateral petals slightly overlapping the dorsal sepal and moderately overlapping the lateral sepals; lateral sepals moderately overlap one another.

*Aspect*.—Flowers are outward-facing to slightly nodding.

*Vertical height*.—Approximately 9.9 cm.

*Diameter*.—Approximately 9.1 cm.

*Depth*.—Approximately 3.0 cm.

*Fragrance*.—No fragrance.

*Lastingness*.—3 weeks, on average.

*Persistent*.—Self-cleaning.

*Petals*.—Quantity of Petals — Three unfused petals; two conventional petals and one labellum. Arrangement — One lateral petal on each side. Length — Approximately 5.2 cm. Width — Approximately 4.2 cm. Shape — Broad ovate. Apex — Obtuse. Base — Cuneate. Margin — Entire; moderately to highly undulated. Pubescence, texture and luster of upper surface — Glabrous, velvety and matte. Pubescence, texture and luster of lower surface — Glabrous, velvety and matte. Color when opening, upper surface — Yellow, nearest to RHS 4C, and suffused with a darker shade of yellow towards the apex, nearest to RHS 8B; heavily dotted greyed-purple, nearest to RHS 183B; base of the petal is heavily suffused with greyed-purple, nearest to RHS 185A. Color when opening, lower surface — Yellow, nearest to RHS 4C, and suffused with a darker shade of yellow towards the apex, nearest to RHS 8B; lightly dotted greyed-purple at the margins, nearest to RHS 183B. Color when fully opened, upper surface — Yellow, nearest to RHS 4C, and suffused with greyed-yellow towards the apex, nearest to RHS 160A; heavily dotted greyed-purple, in between RHS 187C and 187D; base of the petal is heavily suffused with greyed-purple, nearest to RHS 185A. Color when fully opened, lower surface — Yellow, nearest to RHS 4D, and suffused with greyed-yellow towards the apex, in between RHS 160A and 161A; lightly dotted greyed-purple at the margins, nearest to RHS 183B. Fading, upper surface — Not fading. Fading, lower surface — Not fading. Venation — Densely reticulate. Venation color, fully opened, upper surface — Yellow, nearest to RHS 5D, and suffused with greyed-yellow towards the apex, nearest to RHS 160A; heavily dotted greyed-purple, in between RHS 187C and 187D. Venation color, fully opened, lower surface — Yellow, nearest to RHS 4D, and suffused with greyed-yellow towards the apex, in between RHS 160A and 161A; lightly dotted greyed-purple at the margins, nearest to RHS 183B.

*Labellum*.—Shape — Three-lobed; the shape of the lateral lobes is reniform, and the aspect is involute; the shape of the central lobe is ovate, and the aspect is convex. Length — Central lobe — Approximately 1.9 cm. Lateral lobes — Approximately 0.7 cm. Width — Central lobe — Approximately 1.6 cm. Lateral lobes — Approximately 0.8 cm. Apex — Central lobe — Strongly emarginate to nearly cleft. Lateral lobes — Broadly obtuse. Base — Central lobe — Cuneate. Lateral lobes — Cuneate. Margin — Central lobe — Entire; moderately undulated. Lateral lobes — Entire; not undulate. Texture and luster of upper surface — Central lobe — Glabrous, velvety, and matte. Lateral lobes — Glabrous, velvety, and matte. Texture and luster of lower surface — Central lobe — Glabrous, velvety, and matte. Lateral lobes — Glabrous, velvety, and matte. Color when opening, upper surface — Central lobe — Greyed-red, nearest to RHS 178B, and margined greyed-orange, a mixture of RHS 164A and 164C. Lateral lobes — Yellow, nearest to RHS 4B, and blotched yellow-orange at the base, in between RHS 14A and 14B. Color when opening, lower surface — Central lobe — Greyed-orange, nearest to RHS 173A, and fading to greyed-yellow towards the base, nearest to RHS 160B; margined greyed-orange, nearest to RHS 164C. Lateral lobes — Yellow, in between RHS 5C and 5D. Color when fully opened, upper surface — Central lobe — Greyed-red, nearest to RHS 178B; fading to a slightly lighter shade of greyed-red at the apex, nearest to RHS 176A, and margined greyed-orange, a mixture of RHS 164A and 164C. Lateral lobes — Yellow, nearest to RHS 5C, and blotched greyed-orange at the base, in between RHS 163A and 163B. Color when fully opened, lower surface — Central lobe — Greyed-orange, nearest to RHS 173A, and fading to greyed-yellow towards the base, nearest to RHS 160B; margined greyed-orange, nearest to RHS 164C. Lateral lobes — Yellow, nearest to RHS 5C, and suffused with a slightly darker shade of yellow at the base, nearest to RHS 9B. Fading, upper surface — Not fading. Fading, lower surface — Not fading. Venation — No visible venation. Venation color, fully opened, upper surface — Central lobe — No visible venation. Lateral lobes — No visible venation. Venation color, fully opened, lower surface — Central lobe — No visible venation. Lateral lobes — No visible venation.

*Callosities*.—Dimensions — 1.3 cm long and 0.6 cm wide, on average. Color — Yellow, nearest to RHS 4C; greyed-red towards the apex of the central lobe, nearest to RHS 178B.

*Spurs*.—Quantity — Average of 1. Length — Approximately 0.6 cm. Diameter — Approximately 0.4 cm. Vertical height — Approximately 0.4 cm, at the base. Shape — Short triangular. Apex — Bluntly acute. Base — Broad cuneate. Pubescence, texture and luster — Glabrous, smooth, and matte. Color — Yellow, nearest to RHS 8C; striped a slightly darker shade of yellow, nearest to RHS 11A.

*Sepals*.—Quantity — Average of 3 unfused sepals. Arrangement — One dorsal sepal and two lateral sepals. Length — Dorsal sepal — Approximately 4.8 cm. Lateral sepals — Approximately 4.8 cm. Width — Dorsal sepal — Approximately 4.5 cm. Lateral sepals — Approximately 5.3 cm. Shape — Dorsal sepal — Ovate. Lateral sepals — Reniform to near orbicular. Apex — Dorsal sepal — Retuse. Lateral sepals — Obtuse. Base — Dorsal sepal — Cuneate. Lateral sepals — Cuneate. Margin — Dorsal sepal — Entire; very slightly undulated. Lateral sepals — Entire; moderately undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — Yellow, nearest to RHS 4C, and suffused with a darker shade of yellow towards the apex, nearest to RHS 8B; heavily dotted and striped greyed-purple, nearest to RHS 183B; base of the sepal is heavily suffused with greyed-purple, nearest to RHS 185A. Lateral sepals — Yellow, nearest to RHS 8C, and suffused with a yellow-green towards the apex, in between RHS 145A and 145B; heavily dotted and striped greyed-purple, in between RHS 183A and 183B; base of the sepal is heavily suffused with greyed-purple, nearest to RHS 185A. Color when opening, lower surface — Dorsal sepal — Yellow, nearest to RHS 4C, and suffused with a darker shade of yellow towards the apex, nearest to RHS 8B; lightly dotted greyed-purple at the margins, nearest to RHS 183B, and a large greyed-orange blotch below the apex, nearest to RHS 177C. Lateral sepals — Yellow-green, nearest to RHS 151D, and fading to a lighter shade of yellow-green towards to apex, nearest to RHS 151A; lightly dotted at the margins, nearest to RHS 185A. Color when fully opened, upper surface — Dorsal sepal — Yellow, nearest to RHS 5D, and suffused with greyed-yellow towards the apex, nearest to RHS 160A; heavily dotted greyed-purple, in between RHS 187C and 187D; base of the petal is heavily suffused with greyed-purple, nearest to RHS 185A. Lateral sepals — Yellow, nearest to RHS 8C, and suffused with yellow-green towards the apex, in between RHS 151A and 151B; heavily dotted and striped greyed-red, nearest to RHS 181B; base of the sepal is heavily suffused with greyed-purple, nearest to RHS 185A. Color when fully opened, lower surface — Dorsal sepal — Yellow, nearest to RHS 4C, and suffused with a darker shade of yellow towards the apex, nearest to RHS 8B; lightly dotted greyed-purple at the margins, nearest to RHS 183B, and a large greyed-orange blotch below the apex, nearest to RHS 177C. Lateral sepals — Yellow-green, in between RHS 152D and 153D, and fading to a lighter shade of yellow-green towards to apex, nearest to RHS 151A; lightly dotted at the margins, nearest to RHS 185A. Fading, upper surface — Not fading. Fading, lower surface — Not fading. Venation — Densely reticulate. Venation color, fully opened, upper surface — Dorsal sepal — Greyed-purple, in between RHS 183A and 183B. Lateral sepals — Greyed-purple, in between RHS 183A and 183B. Venation color, fully opened, lower surface — Dorsal sepal — Yellow, nearest to RHS 4C, and suffused with a darker shade of yellow towards the apex, nearest to RHS 8B; large greyed-orange blotch below the apex, nearest to RHS 177C. Lateral sepals — Yellow-green, in between RHS 152D and 153D, and fading to a lighter shade of yellow-green towards to apex, nearest to RHS 151A.

*Pedicels*.—Length — Approximately 5.6 cm. Diameter — Approximately 0.5 cm. Angle — Approximately 110 degree angle to peduncle axis. Strength — Moderate. Texture — Glabrous, axially angled with 5 "ribs", axially twisted (due to resupination). Luster — Glossy. Color — White, RHS N155B, and suffused with greyed-purple, nearest to RHS 186D.

*Bract*.—Quantity — One bract present at the base of each pedicel. Shape — Ovate; folded around the base of each pedicel. Dimensions — Average of 1.3 cm long and 1.4 cm wide. Apex — Broad acute. Base — Broad cuneate. Margins — Entire. Color, both surfaces — Yellow-green, nearest to RHS N144C.

Reproductive organs:

*Column*.—Length — Approximately 0.7 cm. Diameter — Approximately 0.6 cm. Color — Yellow, nearest to RHS 5B.

*Ovary*.—Position — Inferior. Diameter — Approximately 0.2 cm. Color — Yellow-green, nearest to RHS 150D.

*Pollinia color*.—Yellow-orange, nearest to RHS 14B.

Seed and fruit: No fruit and seed production has been detected to date.

Comparison With the Parent Plants

Plants of the new cultivar 'SPCDW1524' differ from the *Vanda* seed parent, 'YSRBPM' (not patented), by the characteristics described in Table 1.

TABLE 1

| Characteristic | 'SPCDW1524' | 'YSRBPM' |
|---|---|---|
| Plant size. | Smaller than 'YSRBPM'. | Larger than 'SPCDW1524'. |
| Flower habit. | More floriferous than 'YSRBPM'. | Less floriferous than 'SPCDW1524'. |
| Flower size. | Larger than 'YSRBPM'. | Smaller than 'SPCDW1524'. |
| General coloration of the petals and sepals (excluding the overlaid color pattern) when fully opened. | Light orange. | Yellow. |

Plants of the new cultivar 'SPCDW1524' differ from the *Vanda* pollen parent, 'M38BP1' (not patented), by the characteristics described in Table 2.

TABLE 2

| Characteristic | 'SPCDW1524' | 'M38BP1' |
|---|---|---|
| Plant size. | Smaller than 'M38BP1'. | Larger than 'SPCDW1524'. |
| Flower habit. | More floriferous than 'M38BP1'. | Less floriferous than 'SPCDW1524'. |
| Flower size. | Smaller than 'M38BP1'. | Larger than 'SPCDW1524'. |
| General coloration of the petal and sepal color pattern when fully opened. | Dark red. | Pink. |

Comparison With the Most Similar *Vanda* Cultivar Known to the Inventor

Plants of the new cultivar 'SPCDW1524' are most similar to the cultivar, *Vanda* 'SPCDW1203' (U.S. Plant Pat. No. 26,589). A comparison of 'SPCDW1524' with *Vanda* 'SPCDW1203' is described in Table 3.

TABLE 3

| Characteristic | 'SPCDW1524' | 'SPCDW1203' |
|---|---|---|
| General coloration of the petals and sepals (excluding the overlaid color pattern) when fully opened. | Light orange. | Light red-purple. |
| Expression of the color pattern on the lateral sepals when fully opened. | Heavily dotted and striped; appearing to be tessellated. | Moderately dotted and blotched; not appearing to be tessellated. |
| Width of the lateral lobes of the labellum. | Wider than 'SPCDW1203'. | More narrow than 'SPCDW1524'. |
| Central lobe of the labellum; general coloration when fully open. | Greyed-red and margined greyed-orange. | Darker shade of greyed-red. |
| Shape of the central lobe of the labellum. | Ovate. | Triangular. |
| Color of the column. | Yellow. | Light purple. |

That which is claimed is:

1. A new and distinct variety of *Vanda* plant named 'SPCDW1524', substantially as described and illustrated herein.

* * * * *